United States Patent

Wiezer et al.

[11] 4,220,773
[45] Sep. 2, 1980

[54] PROCESS FOR THE MANUFACTURE OF AZA-SPIRODECANES

[75] Inventors: Hartmut Wiezer, Gersthofen; Helmut Korbanka, Adelsried; Norbert Mayer, Gablingen, all of Fed. Rep. of Germany

[73] Assignee: Hoechst Aktiengesellschaft, Fed. Rep. of Germany

[21] Appl. No.: 64,056

[22] Filed: Aug. 6, 1979

[30] Foreign Application Priority Data

Aug. 10, 1978 [DE] Fed. Rep. of Germany ....... 2834962

[51] Int. Cl.² ............................................ C07D 405/04
[52] U.S. Cl. ....................................... 546/19; 546/20
[58] Field of Search ..................... 546/19, 20; 548/216

[56] References Cited

U.S. PATENT DOCUMENTS

| 4,107,139 | 8/1978 | Mayer et al. | 546/19 |
| 4,110,334 | 8/1978 | Mayer et al. | 546/19 |

Primary Examiner—Henry R. Jiles
Assistant Examiner—Robert T. Bond

Attorney, Agent, or Firm—Connolly and Hutz

[57] ABSTRACT

For preparing 1-oxa-diaza-oxo-spirodecanes of the formula

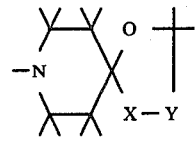

where X≠Y, standing for

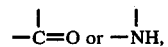

either a polyalkylpiperidone-4-cyanohydrine is reacted with an aldehyde or a ketone, or a polyalkyl-piperidone-4 is reacted with an aldehyde or ketone-cyanohydrine in a liquid aliphatic carboxylic acid as solvent.

3 Claims, No Drawings

PROCESS FOR THE MANUFACTURE OF AZA-SPIRODECANES

1-Oxa-diaza-oxo-spirodecanes are known from German Offenlegungsschriften Nos. 2 634 957 and 2 606 026 as substances which are excellently suitable for stabilizing synthetic polymers, and which are compounds of the formula (I)

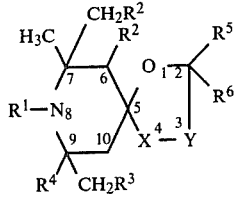

in which
X and Y, being different, each are

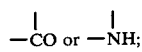
—CO or —NH;

$R^1$ is hydrogen or $C_1$–$C_{12}$-alkyl, preferably hydrogen or $C_1$–$C_4$-alkyl, especially hydrogen;

$R^2$ and $R^3$, either are identical and represent each hydrogen or a $C_1$–$C_5$-alkyl group, preferably hydrogen or a methyl group, especially hydrogen, $R^4$ being a methyl group in this latter case, or $R^2$ is hydrogen or $C_1$–$C_5$-alkyl, and $R^3$ and $R^4$, together with the carbon atoms to which they are linked, form a $C_5$- or $C_6$-cycloalkyl group, or a group of the formula

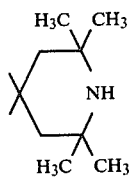

$R^5$ is hydrogen, $C_1$–$C_{30}$-alkyl, preferably $C_1$–$C_8$-alkyl, especially $C_1$–$C_5$-alkyl, a phenyl or naphthyl group being unsubstituted or substituted by chlorine or $C_1$–$C_4$-alkyl, preferably the first cited group, or a $C_7$–$C_{12}$-phenylalkyl group being unsubstituted or substituted by $C_1$–$C_4$-alkyl, preferably a benzyl group;

$R^6$ is hydrogen, $C_1$–$C_{30}$-alkyl, preferably $C_1$–$C_{18}$-alkyl, especially $C_1$–$C_{13}$-alkyl, an unsubstituted phenyl or naphthyl group, preferably a phenyl group, a $C_7$–$C_{12}$-phenylalkyl group being unsubstituted or substituted by $C_1$–$C_4$-alkyl, preferably a benzyl group; or $R^5$ and $R^6$, together with the carbon atom linked to them are a $C_5$–$C_{18}$-cycloalkyl group being unsubstituted or substituted by up to four $C_1$–$C_4$-alkyl groups, preferably methyl groups, preferably a $C_5$–$C_{12}$-cycloalkyl group or a group of the formula

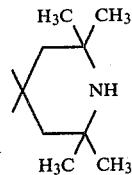

Processes for the manufacture of the cited 1-oxa-diaza-oxo-spirodecanes are specified in the above German Offenlegungsschriften (see also German Offenlegungsschriften No. 1 770 791 and 2 109 333). Starting substances are either piperidone-cyanohydrine which has to be first converted to the carbamoyl compound, and this compound is then reacted with aldehydes or ketones; or piperidone as starting substance is reacted with an alpha-hydroxycarboxylic acid amide which for its part can be synthetized from an aldehyde or ketone by addition of HCN and saponification of the cyanohydrine. These processes have the disadvantage of requiring several complicated reaction steps proceeding partially with unsatisfactory yields, and isolation of the intermediate products, so that the total yield generally is in a range of from 35 to 65% only.

Further processes are known according to which aliphatic or cycloaliphatic, non-basic cyanohydrines are directly reacted with corresponding ketones, while operating in the presence of large amounts of sulfuric acid serving simultaneously as solvent and catalyst. According to this operation mode, oxazolidones can be prepared from cyclohexanone-cyanoanhydrine or acetone-cyanoanhydrine and cyclohexanone (Ducker, Chem. and Ind. 38, (1968), p. 1276). Japanese Pat. No. 4 318 898 proposes to carry out the reaction in the same manner in non-volatile mineral acids such as sulfuric or polyphosphoric acid with addition of solvents such as diethyl ether or toluene, or in a large excess of carbonyl compounds. When, however, 1-oxa-diaza-oxo-spirodecanes are to be prepared according to this methods, the intended reaction is impossible in the case of the latter process, and according to the first operation mode a still larger excess of sulfuric acid is needed in order to maintain in solution the basic starting products being present as sulfuric acid salts during the reaction. Because the total amount of sulfuric acid must be neutralized in order to isolate the products of the process, intolerably large amounts of polluting salts are formed, so that this process, too, is not suitable for the manufacture of 1-oxa-diaza-oxo-spirodecanes on an industrial scale.

It is therefore the object of the invention to provide a technically practicable and economic process for the manufacture of aza-spirodecanes which is free from the disadvantages as described.

In accordance with this invention, there has been found that 1-oxa-diaza-oxo-spirodecanes can be obtained according to the processes of the German Offenlegungsschriften cited, surprisingly with omission of the expensive alpha-hydroxycarboxylic acid amide step, by directly reacting piperidone-cyanohydrine with aldehyde or ketone, or aldehyde- or ketone-cyanohydrine with piperidone, when meeting certain requirements.

The present invention relates therefore to a process for the manufacture of 1-oxa-diaza-oxo-spirodecanes of the formula (I)

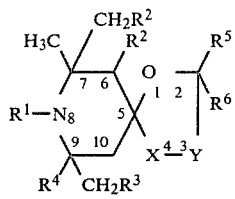

in which X, Y and $R^1$ through $R^6$ are as defined above, which comprises reacting a polyalkyl-piperidone-4-cyanohydrine of the formula (II)

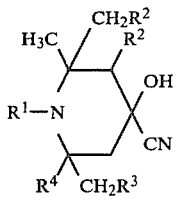

with an aldehyde or ketone of the formula (III)

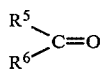

or reacting a polyalkyl-piperidone-4 of the formula (IV)

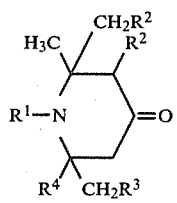

with an aldehyde- or ketone-cyanohydrine of the formula (V)

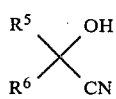

in which formulae the radicals $R^1$ through $R^6$ are as defined above, at a temperature of from 20° to 120° C. in the presence of an aliphatic carboxylic acid liquid at room temperature as solvent, and in the presence of an inorganic protonic acid; the carbonyl compounds (III) and (IV), respectively, being used in a 1- to 3-fold molar amount relative to the cyanohydrines (II) and (V), respectively, and the amount of protonic acid being chosen in such a manner that the piperidone-cyanohydrines (II) and the piperidones (IV), respectively, are present as salts, while the 0.5 to 2-fold molar amount relative to the cyanohydrine to be converted is present in addition, and by subsequently liberating the free base from the protonic acid salt of the intended azaspirodecane so obtained by treatment with a stronger base.

The operation mode of the invention allows to obtain pure azaspirodecanes with good yields, which was not to be expected. On the contrary, it was to be expected that the reaction in the presence of lower aliphatic carboxylic acids would not proceed as desired, because piperidone cyanohydrines can react with themselves under identical reaction conditions in a Ritter reaction, as results from tests carried out by ourselves. It is therefore extremely surprising that there is no formation of by-products in accordance with the invention.

It was furthermore surprising to observe that a successful conversion obviously does not depend on the presence of the starting material in dissolved form in any organic solvent, but on the kind of this solvent. For example, the reaction does not proceed as intended in dimethyl formamide or ethyleneglycol, in which the starting products and certain final products are easily soluble.

According to the invention, piperidone-cyanohydrine (which may alternatively be prepared in situ from piperidone and alkali metal cyanide in a preliminary reaction in the same solvent) and aldehyde, or aldehyde- or ketonecyanohydrine and piperidone are reacted with each other in the presence of the aliphatic carboxylic acid liquid at room temperature which serves as solvent, in which reaction an inorganic protonic acid must be present as catalyst. Suitable aliphatic carboxylic acids are lower fatty acids; acetic acid being preferred. The amount is the 1- to 6-fold, preferably 1.1- to 3-fold, molar amount, relative to the weight of the reactants. Suitable protonic acids are sulfuric acid, phosphoric acid, furthermore hydrogen halides, especially hydrogen chloride. The protonic acid must be added in such an amount that the basic reactants are present in the form of their salts, and that the 0.5- to 2.0-fold, preferably 0.7- to 1.5-fold, molar amount of protonic acid, relative to the cyanohydrine used, is present in addition as catalyst. In the case of gaseous protonic acid, the excess to be chosen must be even larger (1- to 10-fold molar amount, relative to cyanohydrine), and the reaction is advantageously carried out under pressure, which may be up to 25 bars.

The reaction temperature is in a range of from 20° to 120° C., preferably 20° to 90° C., when using aldehydes of the formula (III) especially from 20° to 60° C., in the case of ketones of the formula (III) and (IV), respectively, especially from 50° to 90° C. The reaction time is from 5 to 60, preferably 10 to 40, and especially 15 to 30, hours.

After completed reaction, the intended aza-spirodecanes are present in the form of their protonic acid salts, some of which, being already crystallized, can be obtained by filtration. When the salts are still in dissolved state, they can be isolated by precipitation with nonsolvents, for example ether or acetone. Alternatively, the reaction solutions may be concentrated and worked up.

The free bases are obtained from the salts by neutralization with stronger bases such as ammonia, amine bases, alkali metal hydroxides, alkali metal carbonates or alkali metal alcoholates.

The following examples illustrate the invention.

EXAMPLE 1

2,2,7,7,9,9-Hexamethyl-1-oxa-4,8-diazo-3-oxo-spiro-[4,5]-decane

A mixture of 500 g of glacial acetic acid, 155 g of 2,2,6,6-tetramethyl-piperidone-4, 85 g of acetone-cyanohydrine and 200 g of concentrated $H_2SO_4$ (to be added last) is stirred for 25 hours at 70° C. in a 1 liter glass flask. After cooling, the reaction mixture is suction-filtered and the solids are washed twice with 130 ml each of acetone, until they are free from glacial acetic acid. 234 g=69% of th. of the sulfuric acid salt of the intended compound are obtained.

EXAMPLE 2

2,2,7,7,9,9-Hexamethyl-1-oxa-3,8-diazo-4-oxo-spiro-[4,5]-decane

In analogy to Example 1, 500 g of glacial acetic acid, 116 g of acetone, 182 g of 2,2,6,6-tetramethyl-4-hydroxy-4-cyanopiperidine and 200 g of concentrated $H_2SO_4$ are reacted. 254 g=75 of th. of the sulfuric acid salt of the intended compound are obtained.

EXAMPLE 3

2-iso-Octyl-7,7,9,9-tetramethyl-1-oxa-3,8-diaza-spiro-[4,5]-decane 182 g of 2,2,6,6-tetramethyl-4-hydroxy-4-cyanopiperidine, 284 g of isononyl-aldehyde and 200 g of concentrated sulfuric acid are stirred for 25 hours at 60° C. in 600 g of glacial acetic acid in a 2 liter apparatus with agitator. After cooling the main portion of the solvent is distilled off under reduced pressure. The residue is stirred with 500 ml of acetone and suction-filtered, thus yielding 292 g=69% of th. of the sulfuric acid salt of the intended compound.

EXAMPLE 4

2,2,4,4-Tetramethyl-3,14-diaza-7-oxa-15-oxo-dispiro-[5,1,5,2]-pentadecane 182 g of 2,2,6,6-tetramethyl-4-hydroxy-4-cyanopiperidine, 200 g of cyclohexanone, 500 g of glacial acetic acid and 200 g of concentrated sulfuric acid are stirred for 26 hours at 60° C. in a 1 liter apparatus provided with agitator. After cooling, the mixture is suction-filtered and washed twice with 130 ml each of acetone, thus yielding 278 g=75% of th. of the sulfuric acid salt of the intended compound.

EXAMPLE 5

2,2,4,4,10,10,12,12-Ocatmethyl-3,14-diaza-7-oxa-15-oxo-dispiro-[5,1,5,2]-pentadecane 14.6 g of 2,2,6,6-tetramethyl-4-hydroxy-4-cyanopiperidine, 18.8 g of 3,3,5,5-tetramethyl-cyclohexanone and 15.9 g of concentrated sulfuric acid are stirred for 23 hours at 70° C. in 120 ml of glacial acetic acid in a 250 ml apparatus with agitator. After cooling, the mixture is suction-filtered, washed with acetone and dried, thus yielding 20 g=56% of th. of the sulfuric acid salt of the intended compound.

EXAMPLE 6

2,2,4,4,10,12-Hexamethyl-3,14-diaza-7-oxa-15-oxo-dispiro-[5,1,5,2]-pentadecane 18.2 g of 2,2,6,6-tetramethyl-4-hydroxy-4-cyanopiperidine, 12.9 g of 3,5-dimethyl-cyclohexanone, 150 ml of glacial acetic acid and 19.6 g of concentrated sulfuric acid are heated for 43 hours at 70° C. in a 250 ml apparatus provided with agitator. After cooling, 23 g=74.5% of th. of sulfuric acid salt of the intended compound are obtained.

EXAMPLE 7

2,7,7,9,9-Pentamethyl-2-octadecyl-1-oxa-3,8-diaza-4-oxo-spiro-[4,5]-decane 42 g=73% of th. of the sulfuric acid salt of the intended compound are obtained in analogy to Example 6 from 18.2 g of 2,2,6,6-tetramethyl-4-hydroxy-4-cyanopiperidine and 44.4 g of eicosanone-2.

EXAMPLE 8

2,2,4,4-Tetramethyl-3,20-diaza-7-oxa-21-oxa-dispiro-[5,1,11,2]-heneicosane 100 g of 2,2,6,6-tetramethyl-4-hydroxy-4-cyanopiperidine, 120 g of cyclododecanone, 300 g of glacial acetic acid and 94.5 g of concentrated sulfuric acid are agitated for 25 hours at 80° C. in a 1 liter apparatus with agitator. After cooling, 207 g=82% of th. of the sulfuric acid salt of the intended compound are obtained. For isolating the free base, 100 g of the sulfuric acid salt is boiled for 2 hours with agitation in 500 ml of ethanol containing 15 g of sodium as alcoholate. The alcohol is distilled off, the residue is agitated with 300 ml of water, and the solids are then suction-filtered. Yield: 68.5 g=88% of th., relative to the salt. M.p. 226°–228° C.

EXAMPLE 9

The compound of Example 8 can be prepared alternatively in the following manner:

77.5 g of 2,2,6,6-tetramethyl-piperidone are dissolved in 300 g of glacial acetic acid, and subsequently, 33 g of potassium cyanide are added, whereby the temperature rises to about 50° C. Agitation is continued for 3 hours at this temperature, and, after cooling to room temperature, excess hydrogen cyanide is driven out by means of nitrogen. Subsequently, 100 g of cyclododecanone and 150 g of concentrated sulfuric acid are added, and the batch is agitated for 30 hours at 70° C. The glacial acetic acid is then distilled off under slightly reduced pressure, and the residue is suspended in 1 liter of water. 240 g of 50% NaOH are subsequently added, and agitation is continued for ½ hour at 80° C. After suction-filtration, the product is washed with water and acetone, and 115 g=63% of th. of the intended product in the form of the free base are obtained.

EXAMPLE 10

In this example, the compound of Example 8 is prepared with the use of a gaseous protonic acid.

600 g of glacial acetic acid, 127.4 g of 2,2,6,6-tetramethyl-4-hydroxy-4-cyanopiperidine and 255 g of cyclododecanone are introduced into a 4 liter pressure apparatus. Subsequently, gaseous hydrogen chloride is applied up to a pressure of 3 bars, and the batch is then heated for 26 hours at 70° C., whereby a pressure of about 9 bars establishes itself. After cooling, the product is suction-filtered. 187 g=67% of th. of the HCl salt of the intended compound are obtained.

EXAMPLE 11

2,7,7,9,9-Pentamethyl-2-undecyl-1-oxa-3,8-diaza-4-oxo-spiro-[4,5]-decane

This compound is obtained in analogy to Example 6 from 18.2 g of 2,2,6,6-tetramethyl-4-hydroxy-4-cyanopiperidine and 25 g of tridecanone-2. 26.2 g=54.5% of th. of the sulfuric acid salt of the intended compound are obtained.

EXAMPLE 12

2,2-Dimethyl-7,7,9,9-tetramethyl-1-oxa-3,8-diaza-4-oxo-spiro-[4,5]-decane

The compound is prepared in analogy to Example 6 from 18.2 of 2,2,6,6-tetramethyl-4-hydroxy-4-cyanopiperidine and 34 g of dipentylketone, thus obtaining 31.8 g=71% of th. of the sulfuric acid salt of the intended compound.

EXAMPLE 13

7,7,9,9-Tetramethyl-2,2'dichlorophenyl-1-oxa-3,8-diaza-4-oxo-spiro-[4,5]-decane 18.2 g of 2,2,6,6-tetramethyl-4-hydroxy-4-cyanopiperidine, 31 g of 2,4-dichlorobenzaldehyde and 20 g of concentrated sulfuric acid are stirred in 100 g of glacial acetic acid for 47 hours at 60° C. Subsequently, the batch is sucation-filtered, washed with acetone and dried, thus obtaining 27 g=58.1% of th. of the sulfuric acid salt of the intended compound.

EXAMPLE 14

2,2,4,4-Tetramethyl-7-oxa-14-oxo-3,15-diaza-dispiro-[5,1,5,2]-pentadecane

The sulfuric acid salt of the intended compound is prepared by reacting 31 g of 2,2,6,6-tetramethyl-piperidine with 25 g of cyclohexanone-cyanohydrine at 70° C. in the presence of 40 g of concentrated sulfuric acid and 150 g of glacial acetic acid. Reaction time: 40 hours. Yield of sulfuric acid salt: 41.5 g=61.4% of th.

EXAMPLE 15

7,7,9,9-Tetramethyl-2,2-dibenzyl-1-oxa-3,8-diaza-4-oxo-spiro-[4,5]-decane 18.2 g of 2,2,6,6-tetramethyl-4-hydroxy-4-cyanopineridine, 40 g of dibenzylketone and 20 g of concentrated sulfuric acid are introduced into 100 g of glacial acetic acid and stirred for 48 hours at 75° C. Subsequently, the batch is concentrated, suspended in acetone and suction-filtered. 29.9 g=61.0% of th. are obtained in the form of the sulfuric acid salt.

What is claimed is:

1. A process for the manufacture of aza-spirodecanes of the formula (I)

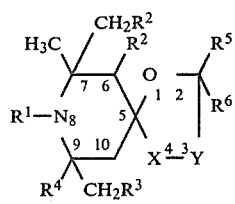

in which

X and Y, being different, each are

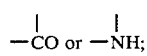
—CO or —NH;

$R^1$ is hydrogen or $C_1-C_{12}$-alkyl
$R^2$ and $R^3$, either are identical and represent each hydrogen or a $C_1-C_5$-alkyl group
$R^4$ being a methyl group in this case, or $R^2$ is hydrogen or $C_1-C_5$-alkyl, and $R^3$ and $R^4$, together with the carbon atoms to which they are linked, form a $C_5$- or $C_6$-cycloalkyl group, or a group of the formula

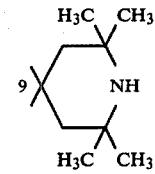

$R^5$ and $R^6$ being identical or different, each are hydrogen, $C_1-C_{30}$alkyl, a phenyl or naphthyl group being unsubstituted or substituted by chlorine or $C_1-C_4$-alkyl, or a phenylalkyl group being unsubstituted or substituted by $C_1-C_4$-alkyl; or $R^5$ and $R^6$, together with the carbon atom linked to them are a $C_5-C_{18}$-cycloalkyl group being unsubstituted or substituted by up to four $C_1-C_4$-alkyl groups, or a group of the formula

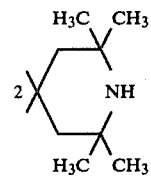

which comprises reacting a polyalkyl-piperidone-4-cyanohydrine of the formula (II)

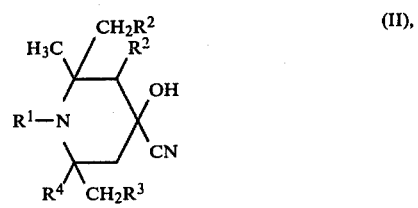

with an aldehyde or ketone of the formula (III)

or reacting a polyalkyl-piperidone-4 of the formula (IV)

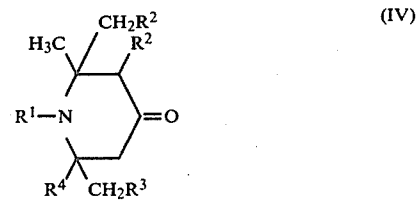

with an aldehyde- or ketone-cyanohydrine of the formula (V)

at a temperature of from 20° to 120° C. in the presence of an aliphatic carboxylic acid liquid at room temperature as solvent, and in the presence of an inorganic protonic acid; the carbonyl compounds (III) and (IV), respectively, being used in a 1- to 3-fold molar amount relative to the cyanohydrines (II) and (V), respectively, and the amount of protonic acid being chosen in such a manner that the piperidone-cyanohydrines (II) and the piperidones (IV), respectively, are present as salts, while the 0.5 to 2-fold molar amount relative to the cyanohydrine to be converted is present in addition, and by subsequently liberating the free base from the protonic acid salt of the intended azaspirodecane so obtained by treatment with a stronger base.

2. The process as claimed in claim 1, wherein the aliphatic carboxylic acid serving as solvent is acetic acid.

3. The process as claimed in claim 1, wherein the inorganic protonic acid is sulfuric acid or gaseous hydrogen chloride.

* * * * *